United States Patent [19]

Kump

[11] Patent Number: 4,918,066
[45] Date of Patent: Apr. 17, 1990

[54] SUBSTITUTED 4-BENZYLPIPERAZINYL COMPOUNDS

[75] Inventor: Wilhelm Kump, Biel-Benken, Switzerland

[73] Assignee: Ciba-Geigy Corporation, Ardsley, N.Y.

[21] Appl. No.: 296,903

[22] Filed: Jan. 11, 1989

Related U.S. Application Data

[63] Continuation of Ser. No. 68,289, filed as PCT CH85/00155 on Oct. 18, 1985, published as WO87/02361 on Apr. 23, 1987, abandoned.

[51] Int. Cl.$^4$ ............... A61K 31/395; C07D 521/00
[52] U.S. Cl. ..................... 514/183; 540/458; 540/459
[58] Field of Search ............... 540/458, 459; 514/183

[56] References Cited

U.S. PATENT DOCUMENTS

| | | | |
|---|---|---|---|
| 3,342,810 | 9/1967 | Maggi et al. | 260/239.3 |
| 3,796,798 | 6/1971 | Lancini et al. | 424/180 |
| 4,002,752 | 1/1977 | Cricchio et al. | 424/250 |
| 4,002,754 | 1/1977 | Cricchio et al. | 424/250 |
| 4,005,077 | 1/1977 | Bickel et al. | 540/459 |
| 4,193,920 | 3/1980 | Konstantinova et al. | 260/239.3 P |
| 4,551,450 | 11/1985 | Traxler | 514/183 |
| 4,681,938 | 7/1987 | Traxler | 540/458 |

OTHER PUBLICATIONS

The Journal of Antibiotics vol. 24, No. 1 pp. 64–66 (1971).
The Merck Index 10th Ed. Abstract 8113 p. 1187.
Journal of the National Cancer Institute vol. 49 No. 1, pp. 61–79 (1972).
Journal of Medicinal Chem. vol. 16 No. 10 pp. 1071–1075 (1973).
CA 107: 108862z (1987).
Chemical Abstracts vol. 108, (1988) Item 150,158, abstracting South African Patent ZA 85 08 167, Jun. 24, 1987.

Primary Examiner—Robert T. Bond
Attorney, Agent, or Firm—JoAnn Villamizar

[57] ABSTRACT

3-W-Rifamycin SV and S compound, wherein W is a piperazin-1-yl radical of the formula

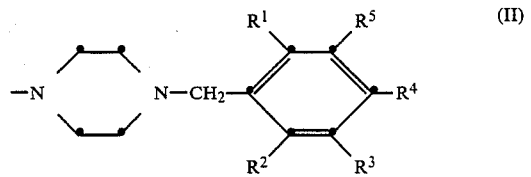

wherein $R^1$ and $R^2$ are $C_1$–$C_4$alkyl and $R^3$, $R^4$ and $R^5$ are hydrogen or $C_1$–$C_4$alkyl, or $R^2$ together with $R^3$ or $R^3$ together with $R^4$ are buta-1,3-dien-1,4-ylene, trimethylene or tetramethylene, each of which is unsubstituted or substituted by $C_1$–$C_4$alkyl, and $R^1$, $R^4$ and $R^5$ or $R^1$, $R^2$ and $R^5$ are hydrogen or $C_1$–$C_4$alkyl, and salts thereof, have long-term antituberculotic and antimicrobial activity.

9 Claims, No Drawings

SUBSTITUTED 4-BENZYLPIPERAZINYL COMPOUNDS

This application is a continuation of application Ser. No. 068,289, filed as PCT CH85/00155 on Oct. 18, 1985, published as WO87/02361 Apr. 23, 1987, now abandoned.

The present invention relates to novel derivatives of rifamycin SV and rifamycin S with pronounced antibiotic activity. These novel derivatives are rifamycin compounds which are substituted in the 3-position by a substituted piperazin-1-yl radical and which are characterised by the formula

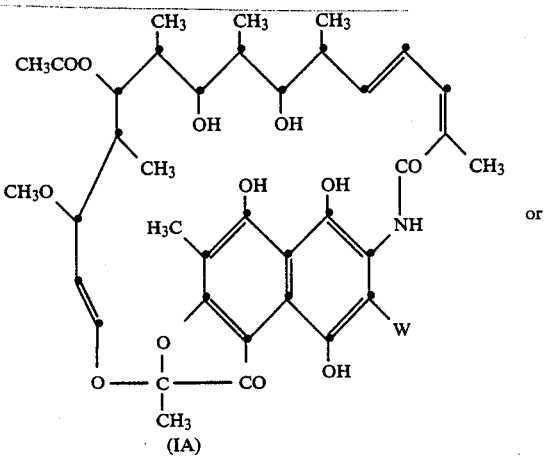

(IA)

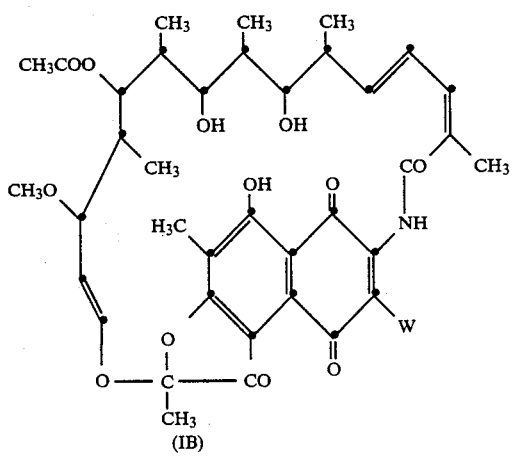

(IB)

wherein W is a piperazin-1-yl radical of the formula

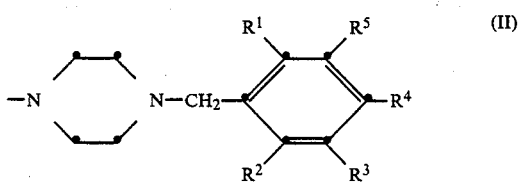

(II)

wherein $R^1$ and $R^2$ are $C_1$–$C_4$alkyl and $R^3$, $R^4$ and $R^5$ are hydrogen or $C_1$–$C_4$alkyl, or wherein $R^2$ together with $R^3$ together with $R^4$ are buta-1,3-dien-1,4-ylene, trimethylene or tetramethylene, each of which is unsubstituted or substituted by $C_1$–$C_4$alkyl, and $R^1$, $R^4$ and $R^5$ or $R^1$, $R^2$ and $R^5$ are hydrogen or $C_1$–$C_4$alkyl, and salts thereof.

The invention also relates to the preparation of the compounds of formulae IA and IB and to the salts thereof, to pharmaceutical compositions containing them, and to the use of said compounds and compositions.

In view of the very close relationship between the 1,4-quinone and 1,4-hydroquinone form (corresponding to rifamycin S and rifamycin SV) and of the ease with which the two forms can be converted into each other, both forms are encompassed by the subject matter of this invention unless otherwise specifically stated; however, the SV form (IA) is the preferred one.

Examples of $C_1$–$C_4$alkyl groups are ethyl, propyl, isopropyl, n-butyl, isobutyl or tert-butyl, but preferably methyl.

Preferred compounds of the present invention are the compounds of formulae (IA) and (IB) wherein W is the radicasl of formula (II), in which $R^1$ and $R^2$ are $C_1$–$C_4$alkyl, preferably methyl, $R^4$ is hydrogen or $C_1$–$C_4$alkyl, e.g. methyl or tert-butyl, and $R^3$ and $R^5$ are hydrogen, or wherein $R^2$ and $R^3$ together or $R^3$ and $R^4$ together are buta-1,3-dien-1,4-ylene, trimethylene or tetramethylene, and $R^1$, $R^4$ and $R^5$ or $R^1$, $R^2$ and $R^5$ are hydrogen, and salts thereof, in particular pharmaceutically acceptable salts thereof.

In particular, the invention relates to compounds of formula IA, wherein W is a radical of formula (II) in which $R^1$ and $R^2$ are $C_1$–$C_4$alkyl, preferably methyl, $R^4$ is hydrogen or $C_1$–$C_4$alkyl, e.g. methyl or tert-butyl, and $R^3$ and $R^5$ are hydrogen, or wherein preferably $R^2$ and $R^3$ together or $R^3$ and $R^4$ together are buta-1,3-dien-1,4-ylene, and $R^1$, $R^4$ and $R^5$ or $R^1$, $R^2$ and $R^5$ are hydrogen, and salts thereof, in particular pharmaceutically acceptable salts thereof.

3-(Piperazin-1-yl)-rifamycin S and 3-(piperazin-1-yl)-rifamycin SV which are substituted in the 4-position of the piperazin-1-yl radical have already been disclosed. For example, U.S. Pat. No. 4,005,077, column 4, lines 3–24, mentions such rifamycin derivatives which may carry in this 4-position an unsubstituted or substituted hydrocarbon radical which may be $C_1$–$C_6$lower alkyl or mono- or dihydroxy-lower alkyl or lower alkoxy, carbalkoxy, phenyl or phenyl-lower alkyl. Among the derivatives carrying such substituents, particular mention is made of benzyl and 1- or 2-phenylethyl derivatives which may be substituted in the aromatic nucleus by one or more radicals, e.g. by $C_1$–$C_6$alkyl.

Substituted 3-(4-benzylpiperazin-1-yl)-rifamycin SV and S carrying substituents of the last mentioned kind are disclosed in particular in Example 77 of the U.S. patent specification referred to above. For example, in addition to 3-(4-benzylpiperazin-1-yl)-rifamycin SV, the following compounds are disclosed in the table of this Example 77: 3-[4-(p-methylbenzyl)-piperazin-1-yl]-rifamycin SV, 3-[4-(o-methylbenzyl)-piperazin-1-yl]-rifamycin SV, 3-[4-(methylbenzyl)-piperazin-1-yl]-rifamycin SV, 3-[4-(p-isopropylbenzyl)-piperazin-1-yl]-rifamycin SV, 3-[4-(2,3-dimethylbenzyl)-piperazin-1-yl]-rifamycin SV and 3-[4-(p-tert-butylbenzyl)-piperazin-1-yl]-rifamycin SV.

All these compounds have a very good antituberculotic activity, as may be demonstrated in mice or rats which have been infected with Mycobacterium tuberculosis bovis. In these tests they have $ED_{50}$ values which correspond more or less to those of the known antituberculotic agent rifampicin.

Although rifampicin is one of the best agents for the treatment of tubercular infections, its relatively short retention time in the organism is sometimes a considerable drawback. The provision of compounds which, in comparison with rifampicin, have an approximately equally potent but more prolonged activity against tubercular infections, is therefore one of the most urgent tasks in this field. The 3-(4-benzylpiperazin-1-yl)-rifamycins disclosed in the above mentioned U.S. Pat. No. 4,005,077 also do not have the desired advantage. They are superior to rifampicin, as stated above, in respect of antituberculotic action in vivo, being about three times more effective, but their long-term activity is scarcely better.

It has now been found that the novel compounds of this invention are surprisingly distinguished not only by good antituberculotic activity, which is about the same as that of rifampicin, but also in particular by an appreciably increased retention time in the organism.

The differences between the prior art compounds and the novel compounds of the present invention may be shown by the data set forth in Table 1. It is clearly evident from the table that the retention time of compounds A and B in the organism is appreciably longer than that of rifampicin or of compounds 1 to 4 of U.S. Pat. No. 4,005,077. This can be especially clearly seen from the comparison of compound A of this invention which is trimethylated in the benzyl nucleus with the monosubstituted anologs of the U.S. patent, i.e. the three monomethylbenzyl derivatives (compounds 1 to 3) on the one hand and a benzyl derivative carrying a larger alkyl substituent, i.e. 3-(4-isopropylpiperazin-1-yl)-rifamycin SV (compound 4) on the other hand.

TABLE 1

Antituberculotic activity and pharmacokinetic properties of the compounds of the invention and a number of prior art compounds.

| 3-(4-R-piperazin-1-yl)-rifamycin SV R | Activity against Mycobacterium tuberculosis TB H$_3$R$_v$ MIC (a) (mcg/ml) | ED$_{50}$ p.o. (mg/kg) | Pharmacokinetics Mice t/2(b) (h) | C$_{max}$(c) (mcg/ml) | Rats t/2(b) (h) | C$_{max}$(c) (mcg/ml) |
|---|---|---|---|---|---|---|
| 1. o-methylbenzyl | 0.001 | 1.4 | 22.9 | 2.69 | 86 | 1.32 |
| 2. m-methylbenzyl | 0.0003 | 1.4 | 11.9 | 3.39 | — | — |
| 3. p-methylbenyl | 0.0001 | 1.2 | 11.5 | 2.28 | — | — |
| 4. p-isopropylbenzyl | 0.003 | 1.5 | 20.4 | 1.81 | — | — |
| 5. isobutyl | 0.0001 | 1.0 | 12.0 | 1.20 | — | — |
| 6. 2-methylallyl | 0.0003 | 1.0 | 21.0 | 1.40 | — | — |
| A. 2,4,6-trimethyl-benzyl | 0.003 | 4 | 47.4 | 2.95 | ~450 | 1.51 |
| B. 1-naphthylmethyl | 0.0003 | 3 | 48.5 | 1.88 | 111 | 1.12 |
| Standard: Rifampicin | 0.003 | 5.9 | 6 | 2.48 | 3.8 | 1.39 |

(a) minimum inhibitory concentration (1 mcg = $1.10^{-5}$ g)
(b) t/2 = half-life of the elimination (h = 1 hour)
(c) C$_{max}$ = maximum concentration in the plasma (1 mcg = $1.10^{-5}$ g)

However, compounds A and B of this invention exhibit such a superior activity in respect of pharmacokinetics not only compared with the known compounds falling under the general designation 3-(4-benzylpiperazin-1-yl)-rifamycin SV and S disclosed in U.S. Pat. No. 4,005,077, column 4, lines 3 to 24, but also quite generally with other 3-piperazinyl-rifamycins such as 3-(4-isobutylpiperazin-1-yl)-rifamycin SV (compound 5) and 3-(4-methylpiperazin-1-yl)-rifamycin SV (compound 6).

The novel compounds of this invention have in addition a surprisingly good activity against other Mycobacteria, in particular against atypical Mycobacteria which have recently been found to an increasing degree in AIDS sufferers and which are considered to be the direct cause of death in these patients. Table II shows that the antimicrobial activity in vitro of compounds A and B of this invention is several times greater than the antimicrobial activity exhibited by rifampicin against a number of atypical Mycobacteria. This excellent activity is especially pronounced in group c, i.e. non-photochromogenic micro-organisms, which are among the most dangerous pathogens of AIDS infections.

TABLE II

Activity (MIC) against atypical Mycobacteria.

| Micro-organism (Mycobacterium) | MIC m mcg/ml Comp. A | Comp. B | Rifampicin |
|---|---|---|---|
| (a) Photochromogenic: | | | |
| M. kansasii K 367 | 0.015 | 0.015 | 0.25 |
| (b) Scotochromogenic: | | | |
| M. scrofulaceum K 1166 | 0.03 | 0.06 | 1 |
| M. xenopei K 716 | 1 | 0.5 | 1 |
| M. aquae K 1165 | 0.03 | 0.03 | 0.25 |
| (c) Non-photochromogenic: | | | |
| M. avium K 536 | 0.5 | 1 | 64 |
| M. intracellular K 653 | 0.125 | 0.25 | 2 |
| M. intracellular K 181 | 0.03 | 0.125 | 0.5 |
| M. intracellular K 653 | 0.125 | 0.25 | 2 |
| M. intracellular K 546 | 0.125 | 1 | 16 |
| M. intracellular K 550 | 0.25 | 1 | 8 |
| M. intracellular K 551 | 0.25 | 1 | 1 |

MIC = minimum inhibitory concentration (1 mcg = $1.10^{-5}$ g)

The novel compounds of the present invention also have good antimicrobial properties against other, in particular gram-positive, micro-orgaisms. Thus in the in vitro assay against Staphylococci such as Staphylococcus aureus K 1098, and against Streptococci such as Streptococcus pyogenes Aronson K 1129, they exhibit inhibitory activity in dosages from about 0.005 μg/ml. In the in vivo assay against e.g. the above-mentioned Staphylococcus, the compounds of this invention are effective in dosages (ED$_{50}$) from about 1 mg/kg, when administered subcutaneously as well as orally.

The compounds of this invention have in addition a broad therapeutic range and exhibit significant toxicity only when administered in high dosage, e.g. in the order of magnitude of 5000 mg/kg. They can therefore be used as medicaments, in particular for the treatment of tubercular and AIDS infections, and allso of other infections such as leprosy or those caused by pyogenic pathogens, e.g. Staphylococci.

The novel compounds of formulae IA and IB can be prepared in a manner known per se, for example by (a) reacting a 3-$R_o$-rifamycin S, wherein $R_o$ is hydrogen or halogen, with an amine of formula H—W (III), or (b) reacting a N'-unsubstituted 3-piperazinylrifamycin S or SV with a compound which is capable of introducing the radical of the formula

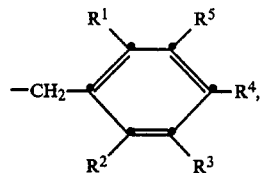
(IV)

into the 4-position of the piperazine radical and, if desired, converting a resultant compound of formula (IA) and/or (IB) into another compound of the formula (IA) and/or (IB) and/or converting a resultant salt into the free compound or into another salt and/or converting a resultant free compound into a salt.

The reaction of rifamycin S ($R_o$=hydrogen) with the amine of formula III can be carried out in a manner which is known per se, for example as described in German patent specification 1 670 377. Thus an excess of amine will conveniently be employed (about 5 to 10 moles). The reaction is conducted e.g. in an organic solvent that does not contain hydroxyl groups and is preferably of low polarity, for example in a halogenated aliphatic hydrocarbon such as methylene chloride or chloroform, an ester or ether, e.g. ethyl acetate, butyl acetate, amyl acetate, cellosolve or tetrahydrofuran and, in particular, dioxane, and preferably at room temperature or, e.g. when the reaction course is slow, at elevated temperature, for example in the temperature range from room temperature to 100° C. The reaction course can be followed by thin-layer chromatography.

Normally in this process variant a mixture of the desired reaction product in both the quinone and hydroquinone form will be obtained. Preferably, as described in more detail below, this mixture is homogenised by producing only the hydroquinone form (derivative of rifamycin SV) by reduction or only the quinone form (derivative of rifamycin S) by oxidation.

Besides 3-chloro- and 3-iodo-rifamycin S (q.v. German patent specification 2 548 128), 3-bromo-rifamycin S can be used in particular as 3-halo-rifamycin S. The replacement of the halogen atom by the radical of the amine of formula III is normally carried out in an inert solvent, preferably in an ether such as tetrahydrofuran or dioxane, or in a halogenated aliphatic hydrocarbon such as chloroform, dichloromethane or 1,2-dichloroethane, or in an aromatic hydrocarbon such as benzene or toluene. It is preferred to carry out the reaction in the temperature range from 0° to 100° C. (q.v. also German Offenlegungsschrift 2 847 427).

In process variant (b), the reagent employed for introducing the radical of formula IV is a reactive ester of the corresponding alcohol, in particular a compound of the formula

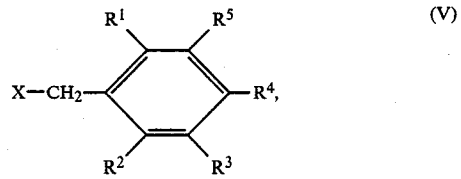
(V)

wherein X is the radical of a strong inorganic or organic acid, e.g. the radical of a hydrohalic acid such as hydrochloric acid, hydrobromic acid or hydriodic acid, of an oxygen-containing inorganic acid such as sulfuric acid, phosphoric acid, phosphorous acid, silicic acid, sulfurous acid, or of a halogenated sulfuric acid such as fluorosulfonic acid, or of an organic sulfonic acid such as an aliphatic or aromatic sulfonic acid, e.g. of a lower alkanesulfonic acid or of a benzenesulfonic acid which may be substituted by lower alkyl or nitro. X is in particular chloro, bromo or iodo, and also methanesulfonyloxy or p-toluenesulfonyloxy.

The reaction is preferably conducted in the presence of a base, in particular of a strongly basic, non-nucleophilic tertiary amine, preferably a suitably sterically hindered aliphatic and/or araliphatic amine such as tri-lower alkylamine, e.g. in the presence of the so-called Hünig base, i.e. ethyldiisopropylamine. The rifamycin compound and the alkylating agent are employed in equimolar amounts, with the base also being preferably added in equimolar amount.

The reaction product is isolated from a reaction mixture as obtained by a process of this invention in a manner which is known per se, e.g. by dilution with water and/or, if desired, by neutralisation with an aqueous acid such as an inorganic or organic acid, e.g. a mineral acid or, preferably, citric acid, and by addition of a wagter-immiscible solvent such as a chlorinated hydrocarbon, e.g. chloroform or methylene chloride, whereupon the reaction product transfers to the organic phase from which it can be obtained in pure form in conventional manner, e.g. by drying, concentrating the solvent and crystallisation, and/or by chromatographying the residue or by other customary methods of purification.

The starting materials for the above described process variants are known or they can be prepared in a manner known per se. Thus, for example, the starting 3-piperazinyl-rifamycin SV can be obtained by the process described in German patent specification 1 676 377 from rifamycin S and piperazine with subsequent reduction of the product with ascorbic acid.

The reaction product can be obtained in the hydroquinone form of formula IA or in the quinone form of formula IB or, especially the product of process variant (a), in the form of a mixture of both compounds. The two forms can be converred in a manner known per se into each other or a mixture of both forms can be converted into one of the two individual forms. The conversion of a quinone of formula IB into the corresponding hydroquinone of formula IA, or of a hydroquinone of formula IA into a quinone of formula IB, or the homogenisation of a mixture of both compounds by reduction or oxidation can be carried out after or, preferably, before the isolation of the desired product. The reduction can be carried out by treatment with, in particular, a reducing agent suitable for reducing a quinone to the corresponding hydroquinone, for example an alkali metal dithionite or hydrosulfite such as socium dithionite or sodium hydrosulfite, zinc and acetic acid, or preferably with ascorbic acid. The oxidation can be carried out by treatment with, in particular, an oxidising agent suitable for converting a hydroquinone into the corresponding quinone, for example atmospheric oxygen, hydrogen peroxide, an alkali metal ferricyanide such as potassium ferricyanide, a persulfate, e.g. ammonium persulfate, or manganese dioxide. The oxidation is preferably carried out under basic conditions. The quinones are normally violet red compounds, whereas the hydroquinones are usually yellowish and crystallise more readily.

The compounds of this invention can form salts, in particular acid addition salts and, most particularly, pharmaceutically acceptable acid addition salts, with inorganic and organic acids. Such acids are for example hydrohalic acids. e.g. hydrochloric and hydrobromic acid, sulfuric acid, phosphoric acid, nitric acid or perchloric acid, or aliphatic, alicyclic, aromatic or heterocyclic carboxylic or sulfonic acids such as formic acid, acetic acid, propionic acid, succinic acid, glycolic acid, lactic acid, malic acid, tartaric acid, citric acid, fumaric acid, maleic acid, hydroxymaleic acid, oxalic acid, pyruvic acid, phenylacetic acid, benzoic acid, p-aminobenzoic acid, anthranilic acid, p-hydroxybenzoic acid, salicylic acid, p-aminosalicyclic acid, embonic acid, methanesulfonic acid, ethanesulfonic acid, hydroxyethanesulfonic acid, ethylenedisulfonic acid, halobenzenesulfonic acid, toluenesulfonic acid, naphthalenesulfonic acids or sulfanilic acid, and also methionine, tryptophane, lysine or arginine, as well as ascorbic acid. Hydroquinone compounds of the formula IA type can also form salts with bases, e.g. alkali metal salts such as sodium salts.

The salts can be prepared in a manner known per se, e.g. by treatment with an acid suitable for salt formation, or with a base, e.g. with the desired base such as ammonia, or with an organic amine, or with a suitable metal hydroxide, carbonate or bicarbonate such as an alkali metal hydroxide, carbonate or bicarbonate, or with a suitable ion exchanger.

The compounds of this invention can also form inner salts, for example by conventional acido-basic titration to the neutral point or isoelectric point, or they can form quaternary ammonium salts, e.g. by treatment with suitable quaternising agents such as reactive esters of lower alkanols with strong acids, for example a hydrohalic acid, sulfuric acid, or a strong organic sulfonic acid.

These salts, or other salts of the novel compounds such as the picrates, can also be used for purifying the compounds of this invention by converting the free compounds into salts, separating these latter and obtaining the free compounds again from the salts. Because of the close relationship between the free compounds and their salts, the references made throughout this specification with respect to the free compounds will also be understood as applying by analogy to the salts thereof.

The invention also relates to those embodiments of the process in which a compound obtained in any stage of the process is used as intermediate and the missing steps are carried out, or a starting material is used in the form of a derivative, e.g. a salt, or is formed under the reaction conditions.

In the process of this invention, it is preferred to use those starting materials which lead to the compounds referred to at the outset as particularly useful.

In view of the above described pharmacological properties of the novel compounds, the present invention also relates to the use of these compounds by themselves alone, i.e. together with adjuvants, or in combination with other active compounds, in particular antibiotics or chemotherapeutic agents, as compositions for the treatment of infections, especially those caused by tubercle bacilli, atypical Mycobacteria, in particular those of AIDS infections, as well as by bacteria and especially coccae such as those already referred to, namely as medicaments as well as disinfectants. When employed as medicaments, the compounds of this invention are administered in therapeutically effective amounts, preferably in the form of pharmaceutical compositions, together with conventional pharmaceutical excipients or adjuvants. Depending on the species, body weight, age and individual condition, and especially depending on the respective sensitivity of the pathogen, daily doses of about 50 to 3000 mg, which in acute cases may be substantially exceeded, are administered e.g. to warm-blooded animals having a body weight of about 70 kg. The present invention accordingly also relates to the corresponding method of medical treatment.

The invention further relates to pharmaceutical compositions which contain the novel compounds as active ingredients, as well as to the preparation thereof.

The pharmaceutical compositions of this invention are for example those for enteral, such as peroral or rectal, administration, as well as for parenteral administration, to warm-blooded animals.

Suitable dosage unit formulations, especially for peroral administration, e.g. dragées, tablets or capsules, contain preferably from about 50 to 500 mg, most preferably from about 100 to 300 mg, of active ingredient, together with pharmaceutically acceptable excipients or adjuvants.

Suitable carriers are in particular fillers such as sugar, for example lactose, saccharose, mannitol or sorbitol, cellulose preparations and/or calcium phosphates, e.g. tricalcium phosphate or calcium biphosphate, and also binders such as starch pastes, e.g. maize, corn, rice or potato starch, gelatin, tragacanth, methyl cellulose and/or polyvinylpyrrolidone, and/or, if desired, disintegrators, such as the above-mentioned starches, also carboxymethyl starch, crosslinked polyvinylpyrrolidone, agar, alginic acid or a salt thereof such as sodium alginate. Adjuncts are in particular glidants and lubricants, for example silica, talc, stearic acid or salts thereof such as magnesium stearate or calcium stearate, and/or polyethylene glycol. Dragée cores provided with suitable coatings which can be resistant to gastric juices, using inter alia concentrated sugar solutions which may contain gum arabic, talc, polyvinylpyrrolidone, polyethylene glycol and/or titanium dioxide, shellac solutions in suitable organic solvents or mixtures or solvents or, for the preparation of coatings which are resistant to gastric juices, solutions of suitable cellulose preparations such as acetylcellulose phthalate or hydroxypropylmethylcellulose phthalate. Dyes or pigments can be added to the tablets or dragée coatings, for example to identify or indicate different dosages of active ingredient.

Further pharmaceutical compositions for oral administration are dry-filled capsules made of gelatin and also soft sealed capsules consisting of gelatin and a plasticiser such as glycerol or sorbitol. The dry-filled capsules can contain the active ingredient in the form of granules, for example in admixture with fillers such as lactose, binders such as starches, and/or glidants such as talc or magnesium stearate, and optionally stabilisers. In soft capsules, the active ingredient is preferably dissolved or suspended in suitable liquids, such as fatty oils, paraffin oil or liquid polyethylene glycols, to which stabilisers can also be added.

Suitable pharmaceutical compositions for rectal administration are e.g. suppositories, which consist of a combination of the active ingredient with a suppository base. Examples of suitable suppository bases are natural or synthetic triglycerides, paraffin hydrocarbons, polyethylene glycols and higher alkanols. It is also possible to use gelatin rectal capsules which contain a combination of the active ingredient with a base material. Suitable base materials are e.g. liquid triglycerides, polyethylene glycols and paraffin hydrocarbons.

Particularly suitable dosage forms for parenteral administration are aqueous solutions of an active ingredient in water-soluble form, for example a water-soluble salt, or aqueous injection suspensions which contain substances which increase the viscosity, for example sodium carboxymethylcellulose, sorbitol and/or dextran, and optionally also stabilisers. The active ingredient, optionally together with adjuvants, may also be in the form of a lyophilisate which is dissolved before parenteral administration by addition of a suitable solvent.

The pharmaceutical compositions of the present invention are obtained in a manner known per se, e.g. by conventional mixing, granulating, sugar-coating, dissolving or lyophilising methods.

Accordingly, tablet and sugar-coated tablet cores for oral administration can be obtained by combining the active ingredients with solid carriers, if desired granulating the resultant mixture, and processing the mixture or granulate, if desired or necessary after the addition of suitable adjuncts, to tablets or sugar-coated tablet cores.

The following Examples illustrate the invention described above but are not intended to limit its scope in any way.

EXAMPLE 1

To a solution of 5 g of 3-bromo-rifamycin S in 50 ml of tetrahydrofuran are added 3 g of 1-(2,6-dimethyl-4-tert-butylbenzyl)-piperazine and the mixture is allowed to stand for 30 minutes at 20° C. The reaction mixture is then acidified with a solution of aqueous citric acid and the reaction product is taken up in methylene chloride. The methylene chloride extract is dried and concentrated by evaporation to leave a dark residue. This residue is dissolved in methanol and aqueous ascorbic acid is added dropwise to the methanolic solution, whereupon yellow crystals of 3-[4-(2,6-dimethyl-4-tert-butylbenzyl)-piperazin-1-yl]-rifamycin SV precipitate. Melting point: 260° C.

EXAMPLE 2

Following the procedure of Example 1, 3 g of 3-bromo-rifamycin S are reacted with 3 g of 1-(2,4,6-trimethylbenzyl)-piperazine to give yellow crystals of 3-[4-(2,4,6-trimethylbenzyl)-piperazin-1-yl]-rifamycin SV with a melting point of 178°–181° C. (partially with decomposition).

To prepare the sodium salt of this compound, equivalent amounts of 3-[4-(2,4,6-trimethylbenzyl)-piperazin-1-yl]-rifamycin SV and sodium bicarbonate are dissolved in a mixture of dioxane and water and the solution is lyophilised.

EXAMPLE 3

Following the procedure of Example 1, 3 g of 3-bromo-rifamycin S are reacted with 3 g of 1-(1-naphthylmethyl)-piperazine to give yellow crystals of 3-[4-(1-naphthylmethyl)-piperazin-1-yl]rifamycin SV with a melting point of 177°–178° C.

The sodium salt is prepared in a manner analogous to that described in Example 2.

EXAMPLE 4

Capsules containing 250 mg of 3-[4-(2,4,6-trimethylbenzyl)-piperazin-1-yl]-rifamycin SV can be prepared as follows:

| Composition (for 1000 capsules): | |
|---|---|
| 3-[4-(2,4,6-trimethylbenzyl)-piperazin-1-yl]-rifamycin SV | 250.0 g |
| maize starch | 50.0 g |
| polyvinylpyrrolidone | 15.0 g |
| magnesium stearate | 5.0 g |
| ethanol | q.s. |

The active ingredient and the maize starch are mixed and the mixture is moistened with a solution of polyvinylpyrrolidone in 50 g of ethanol. The moist mixture is passed through a sieve with a mesh width of 3 mm and dried at 45° C. The dry granulate is passed through a sieve with a mesh width of 1 mm and mixed with 5 g of magnesium stearate. The mixture is filled in 0.320 g portions into two-piece hard gelatine capsules (size 0).

What is claimed is:

1. A compound of the formula

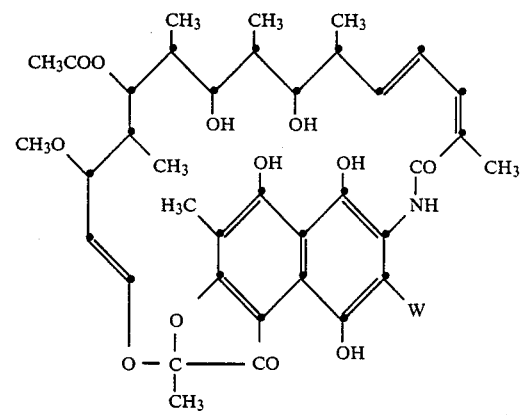

or

-continued

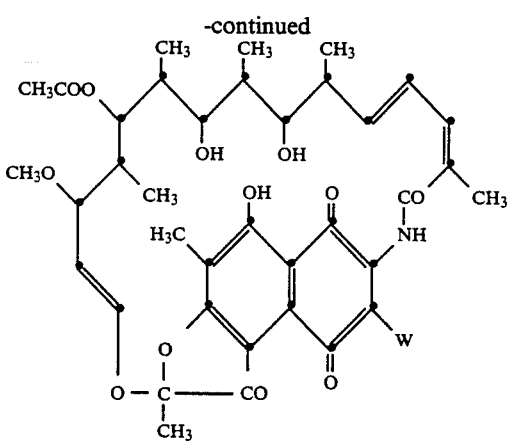

wherein W is a piperazin-1-yl radical of the formula

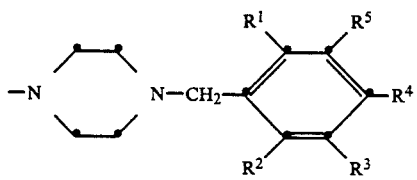 (II)

wherein $R^1$ and $R^2$ are $C_1$–$C_4$alkyl and $R^3$, $R^4$ and $R^5$ are hydrogen or $C_1$–$C_4$alkyl, or $R^2$ together with $R^3$ or $R^3$ together with $R^4$ are buta-1,3-dien-1,4-ylene, trimethylene or tetramethylene, each of which is unsubstituted or substituted by $C_1$–$C_4$alkyl, and $R^1$, $R^4$ and $R^5$ or $R^1$, $R^2$ and $R^5$ are hydrogen or $C_1$–$C_4$alkyl, or a pharmaceutically acceptable salt thereof.

2. A compound according to claim 1 of the formula (IA) or (IB), wherein W is the radical of formula (II), in which $R^1$ and $R^2$ are $C_1$–$C_4$alkyl, $R^4$ is hydrogen or $C_1$–$C_4$alkyl, and $R^3$ and $R^5$ are hydrogen, or wherein $R^2$ and $R^3$ together or $R^3$ and $R^4$ together are buta-1,3-dien-1,4-ylene, trimethylene or tetramethylene, and $R^1$, $R^4$ and $R^5$ or $R^1$, $R^2$ and $R^5$ are hydrogen, or a pharmaceutically acceptable salt thereof.

3. A compound according to claim 1 of the formula (IA), wherein W is a radical of formula (II) in which $R^1$ and $R^2$ are $C_1$–$C_4$alkyl, $R^4$ is hydrogen or $C_1$–$C_4$alkyl and $R^3$ and $R^5$ are hydrogen, or wherein $R^2$ and $R^3$ together or $R^3$ and $R^4$ together are buta-1,3-dien-1,4-ylene, and $R^1$, $R^4$ and $R^5$ or $R^1$, $R^2$ and $R^5$ are hydrogen, or a pharmaceutically acceptable salt thereof.

4. 3-[4-(2,6-Dimethyl-4-tert-butylbenzyl)-piperazin-1-yl]-rifamycin SV or a pharmaceutically acceptable salt thereof.

5. 3-[4-(2,4,6-Trimethylbenzyl)-piperazin-1-yl]-rifamycin SV or a pharmaceutically acceptable salt thereof.

6. 3-[4-(1-Naphthylmethyl)-piperazin-1-yl]-rifamycin SV or a pharmaceutically acceptable salt thereof.

7. An antimicrobial composition containing at least one compound of formula IA or IB as claimed in claim 1, wherein W is as defined in claim 1, or a pharmaceutically acceptable salt thereof.

8. A therapeutic method of combating infectious diseases in man and other warm-blooded animals, which comprises administering an antimicrobially effective dose of a compound as defined in claim 1, alone or together with a pharmaceutical excipient, or in the form of a pharmaceutical composition containing at least one compound of formula IA or IB as claimed in claim 1, wherein W is as defined in claim 1, or a pharmaceutically acceptable salt thereof.

9. An antimicrobial composition according to claim 7 further comprising at least one pharmaceutical excipient.

* * * * *